United States Patent
Blank et al.

(10) Patent No.: US 11,236,070 B2
(45) Date of Patent: Feb. 1, 2022

(54) CHEMICAL PROCESS

(71) Applicant: NOVARTIS AG, Basel (CH)

(72) Inventors: Jarred Blank, Weil am Rhein (DE); Christian Koecher, Rheinfelden (CH); Werner Heinz Pachinger, Basel (CH); Galatea Paredes, Basel (CH); Markus Spaeti, Bottmingen (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/874,613

(22) Filed: May 14, 2020

(65) Prior Publication Data

US 2020/0361903 A1 Nov. 19, 2020

Related U.S. Application Data

(60) Provisional application No. 62/929,995, filed on Nov. 4, 2019, provisional application No. 62/848,869, filed on May 16, 2019.

(51) Int. Cl.
*C07D 401/14* (2006.01)

(52) U.S. Cl.
CPC ................. *C07D 401/14* (2013.01)

(58) Field of Classification Search
CPC .................................................. C07D 401/14
See application file for complete search history.

(56) References Cited

U.S. PATENT DOCUMENTS

| | | | |
|---|---|---|---|
| 5,739,342 A | 4/1998 | Sharma et al. | |
| 8,829,195 B2 * | 9/2014 | Dodd | A61P 43/00 546/275.4 |
| 2019/0360979 A1 | 11/2019 | Anderson et al. | |

FOREIGN PATENT DOCUMENTS

| | | |
|---|---|---|
| CN | 104119238 B | 9/2016 |
| DE | 2117662 A1 | 4/1971 |
| EP | 1674455 A1 | 6/2006 |
| JP | 02104571 A | 4/1990 |
| JP | 02212469 A | 8/1990 |
| JP | 2013095742 A | 5/2013 |
| WO | 1998055453 A1 | 6/1997 |
| WO | 2004096772 A1 | 11/2004 |
| WO | 2006106054 A1 | 10/2006 |
| WO | 2009151991 A | 12/2009 |
| WO | 2012052444 A1 | 4/2012 |
| WO | 2013171639 A1 | 11/2013 |
| WO | 2013171642 A1 | 11/2013 |
| WO | 2016162604 A1 | 10/2016 |
| WO | 2017024167 A1 | 2/2017 |
| WO | 2017039296 A1 | 3/2017 |
| WO | 2020039025 A1 | 2/2020 |

OTHER PUBLICATIONS

Yu et al., "Physical characterization of, etc.," PSTT, vl. 1(3), 118-127). (Year: 1998).*
Braga et al., "Making crystals from . . . " J. Royal Soc. Chem. Commun. p. 3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Ivanisevic et al. "Use of X-ray . . . " Pharm. Sci. Encycl. p. 1-42. (Year: 2010).*
Seddon "Pseudopolymorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Kirk-Othmer Encyclopedia of Chemical Technology, 8, pp. 95-147. (Year: 2002).*
Vippagunta et al., "Crystalline Solids", Advanced Drug Delivery Reviews 48 3-26. (Year: 2001).*
Guillory (in Brittain ed.), "Polymorphism in Pharmaceutical Solids.," NY: Marcel Dekker, Inc., 1-2, 125-181, 183-226. (Year: 1999).*
Wolff, ed., Burger's Medicinal Chemistry and Drug Discovery, 5th edition, NY: John Wiley & Sons, 1996, vol. 1, pp. 949-976.*
"The photooxidation of pyrrole: A simple synthesis of maleimide"; P. de Mayo; Univ Western Ontario, London, Can.; Chemistry & Industry (1962), (No. 35), 1576-7.
"Discovery of Asciminib (ABL001), an Allosteric Inhibitor of the Tyrosine Kinase Activity of BCR-ABL1"; Joseph Schoepfer; Novartis Institutes for BioMedical Research, Basel, CH-4056, Switz.; Journal of Medicinal Chemistry (2018), 61(18), 8120-8135.
"A general synthesis of 5-arylnicotinates"; Wayne J. Thompson; Dep. Chem. Biochem., Univ. California, Los Angeles, CA; Journal of Organic Chemistry (1984), 49(26), 5237-43.
"Synthetic Utilization of Polynitroaromatic Compounds. 1. S-Derivatization of 1-Substituted 2,4,6-Trinitrobenzenes with Thiols"; S. G. Zlotin; et al., Institute of Organic Chemistry, RAS, Moscow, 117913, Russia; Journal of Organic Chemistry (2000), 65(25), 8430-8438.
"Efficient and simple synthesis of 3-aryl-1H-pyrazoles"; Anne-Laure Gerard; Centre d'Etudes et de Recherche sur le Medicament de Normandie, UFR des Sciences Pharmaceutiques, Caen, 14032, Fr.; Tetrahedron Letters (2006), 47 (27), 4665-4669.

* cited by examiner

*Primary Examiner* — Patricia L Morris
(74) *Attorney, Agent, or Firm* — David K. Cheung

(57) ABSTRACT

The present invention provides a novel chemical process for the synthesis of the compound N-[4-(Chlorodifluoromethoxy)phenyl]-6-[(3R)-3-hydroxpyrrolidin-1-yl]-5-(1H-pyrazol-5-yl)pyridine-3-carboxamide.

2 Claims, No Drawings

CHEMICAL PROCESS

CROSS-REFERENCE TO RELATED APPLICATIONS

This application claims the benefit of U.S. Provisional Patent Application No. 62/929,995 filed 4 Nov. 2019 and U.S. Provisional Patent Application No. 62/848,869 filed 16 May 2019. The full disclosures of these applications are incorporated herein by reference in their entirety and for all purposes.

FIELD OF INVENTION

The present invention relates to a novel chemical process for the synthesis of the compound N-[4-(Chlorodifluoromethoxy)phenyl]-6-[(3R)-3-hydroxypyrrolidin-1-yl]-5-(1H-pyrazol-5-yl)pyridine-3-carboxamide.

BACKGROUND OF THE INVENTION

The compound N-[4-(Chlorodifluoromethoxy)phenyl]-6-[(3R)-3-hydroxypyrrolidin-1-yl]-5-(1H-pyrazol-5-yl)pyridine-3-carboxamide, herein also referred as compound of formula (1),

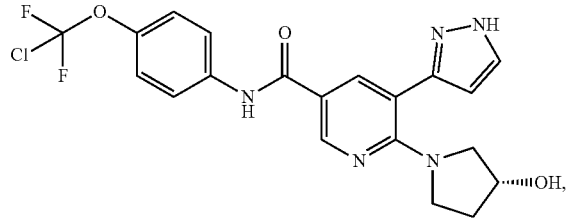

(1)

is a BCR-ABL (breakpoint cluster region-Abelson chimeric protein) tyrosine-kinase inhibitor. WO 2013/171639 A1 provides compounds of Formula (1) as useful in treating diseases which respond to inhibition of the tyrosine kinase enzymatic activity of the Abelson protein (ABL1), the Abelson-related protein (ABL2) and related chimeric proteins, in particular BCR-ABL1. The compound of Formula (1) is also known as (R)—N-(4-(chlorodifluoromethoxy)phenyl)-6-(3-hydroxypyrrolidin-1-yl)-5-(1H-pyrazol-5-yl) nicotinamide, or asciminib.

The compound of Formula (1), preparation of the compound of formula (1), and pharmaceutical compositions of the compound of formula (1) are originally described in WO 2013/171639 A1 as Example 9.

Nevertheless, there remains a need to provide improved processes for the preparation of the compound of formula (1), which are economically more efficient, safer, and better suited for full size production scale.

DESCRIPTION OF THE INVENTION

The present invention is directed to an improved synthesis of compound of formula (1) and its purification, using less hazardous chemicals and/or reaction conditions, generating less waste and providing a reproducible process that is easier to handle on production scale. The present invention is also directed to a more efficient means of generating the compound of formula (1) at higher yield and in higher purity, generates less byproducts, and requires a lower catalyst loading compared to the methods disclosed in the prior art.

In this regard, the present invention is provided in the following aspects.

In accordance with a first aspect of the present invention, there is provided a process for producing the compound of formula (1),

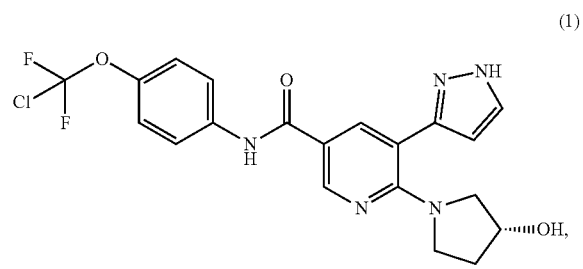 [SMILES: O=C(Nc1ccc(OC(F)(F)Cl)cc1)c1cnc(N2CC[C@@H](O)C2)c(-c2cc[nH]n2)c1]

(1)

or a salt, solvate, stereoisomer, complex, co-crystal, ester, or oxazoline thereof, comprising the step of reacting the compound of formula (2),

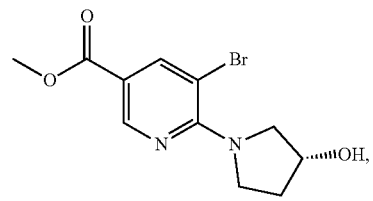

(2)

or a salt, solvate, stereoisomer, complex, co-crystal, ester or oxazoline thereof;
and the compound of formula (3),

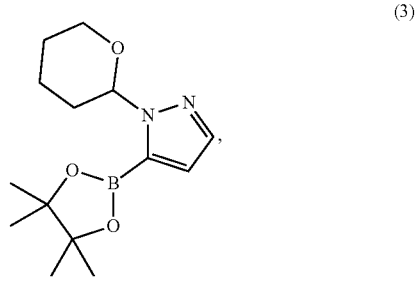 [SMILES: CC1(C)OB(c2ccnn2C2CCCCO2)OC1(C)C]

(3)

or 1-(tetrahydro-2H-pyran-2-yl)-1H-pyrazole-5-boronic acid, pinacol ester with an alkali or alkaline salt in the presence of a metal complex catalyst to obtain the compound of formula (1) or a salt, solvate, stereoisomer, complex, co-crystal, ester or oxazoline thereof, preferably to obtain compound of formula (1) is in its free carboxylic acid form.

In the process, according to first aspect, the metal complex catalyst may be a metal precursor and a ligand or a pre-formed metal complex catalyst comprising a metal M and a ligand.

The metal M may be selected from Cu (copper) and Pd (palladium). Preferably the metal M is Pd.

The metal precursor may be selected from $M(OAc)_2$, $M_2(dba)_3$, $[M(C_3H_5)Cl]_2$ (allyl metal chloride dimer), M(TFA)$_2$, M(MeCN)$_2$Cl$_2$, MCl$_2$, [(cinnamyl)MCl]$_2$, [MCl]$_2$ (metal chloride), and M(acac)$_2$. Preferably the metal precursor is [MCl]$_2$ (metal chloride).

The ligand may be selected from Cy$_3$P, (2-MeOPh)$_3$P, P(tBu)$_2$-n-PrSO$_2$H, Q-phos (1,2,3,4,5-pentaphenyl-1'-(di-tert-butylphosphino)ferrocene), CataCXium ABn (Di(1-adamantyl)benzylphosphine), CataCXium A (Di(1-adamantyl)-n-butylphosphine), and S-Phos (2-Dicyclohexylphosphino-2',6'-dimethoxybiphenyl). Preferably, the ligand is S-Phos.

The pre-formed metal complex catalyst may be composed of the metals as ligands as defined above or is selected from [(o-tol)$_3$P]$_2$PdCl$_2$, [t-Bu$_3$PPdBr]$_2$/Pd-113, (dtbpf)PdCl$_2$/Pd-118, PEPPSI, PdCl$_2$(PPh$_3$)$_2$, Pd(tBu$_2$PhP)$_2$, Pd(dppf)Cl$_2$.CH$_2$Cl$_2$, [(t-Bu)$_3$P]Pd(0), CataCXium C, Pd(tBu$_2$PhP)$_2$ (Pd-122), Pd(dppf)Cl$_2$—CH$_2$Cl$_2$ (Pd-106), (2-MeOPh)$_3$P/Pd$_2$(dba)$_3$, and PdCl$_2$(Amphos)$_2$/Pd-132. Preferably, the pre-formed metal complex catalyst is selected from (dtbpf)PdCl$_2$ (Pd-118), Pd(tBu$_2$PhP)$_2$(Pd-122), Pd(dppf)Cl$_2$—CH$_2$Cl$_2$ (Pd-106) and (2-MeOPh)$_3$P/Pd$_2$(dba)$_3$.

The alkali or alkaline salt may be selected from Na$_2$CO$_3$, Cs$_2$CO$_3$, K$_3$PO$_4$, KF, and K$_2$CO$_3$. Preferably, the alkaline salt is K$_2$CO$_3$.

WO 2013/171639 A1, Example 9 describes a similar process in Stage 9.5 whereby the pre-formed metal complex catalyst Pd(PPh$_3$)$_2$Cl$_2$ and alkali salt K$_3$PO$_4$ in toluene are used to yield intermediate methyl 6-((R)-3-hydroxypyrrolidin-1-yl)-5-(1-(tetrahydro-2H-pyran-2-yl)-1H-pyrazol-5-yl) nicotinate. However, when scaled up to 3 kg, the synthesis resulted in incomplete conversion of starting materials and required additional amounts of the compound of formula (3) and K$_3$PO$_4$ to complete the reaction, thus not suitable for large scale manufacturing of the compound of formula (1).

The reaction provided herein provides a high rate of conversion [>98%, conversion to the compound of formula (1)] and a high purity [>96% purity measured as in-process control (IPC)]. The compound of formula (1) is obtained in high yield (>80%).

An advantage of this process over the prior art process is the reduction of byproducts produced and catalyst loading required for a more complete conversion of starting materials. Therefore, the process of the invention suitable for scaling up for commercial production purposes.

In accordance with a second aspect of the invention, there is provided the process according to first aspect, further comprising the step of reacting the compound of formula (4)

(4)

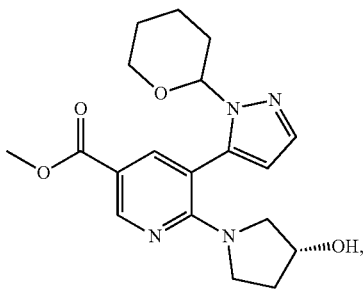

or a salt, solvate, stereoisomer, complex, co-crystal, ester or oxazoline thereof, preferably the compound of formula (4) is in its free methyl ester form; with the compound of formula (5), (5)

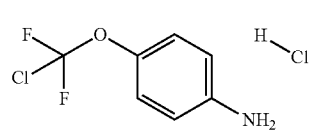

to obtain the compound of formula (6)

(6)

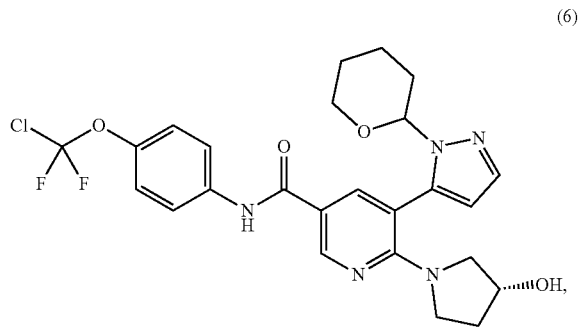 [SMILES: O=C(Nc1ccc(OC(F)(F)Cl)cc1)c1cnc(N2CC[C@@H](O)C2)c(-c2ccnn2C2CCCCO2)c1]

or a salt, solvate, stereoisomer, complex, co-crystal, ester or oxazoline thereof, preferably the compound of formula (6) is in its free carboxylic acid form.

WO 2013/171639 A1, Example 9 describes a similar process in alternate Stage 9.1 by substituting a compound of formula (4) with 6-((R)-3-hydroxypyrrolidin-1-yl)-5-(1-(tetrahydro-2H-pyran-2-yl)-1H-pyrazol-5-yl)nicotinic acid in NMM and combining with HOBt.H$_2$O and EDCl.HCl in THF. However, 6-((R)-3-hydroxypyrrolidin-1-yl)-5-(1-(tetrahydro-2H-pyran-2-yl)-1H-pyrazol-5-yl)nicotinic acid was found difficult to crystallize, extract, and deliver consistent yield from the reaction. The synthesis also resulted in problematic impurities that are difficult to eliminate and negatively impacted yield.

An advantage of the process disclosed herein over the prior art process is that it avoids the problems found with 6-((R)-3-hydroxypyrrolidin-1-yl)-5-(1-(tetrahydro-2H-pyran-2-yl)-1H-pyrazol-5-yl)nicotinic acid and delivers consistent yield of the compound of formula (6). Therefore, the process of the invention is suitable for scaling up for commercial production purposes.

EXAMPLES

Example 1: Step D2+D3→D4

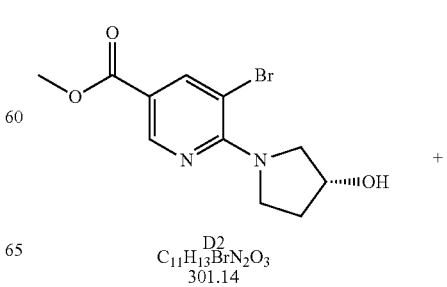

D2
C$_{11}$H$_{13}$BrN$_2$O$_3$
301.14

+

-continued

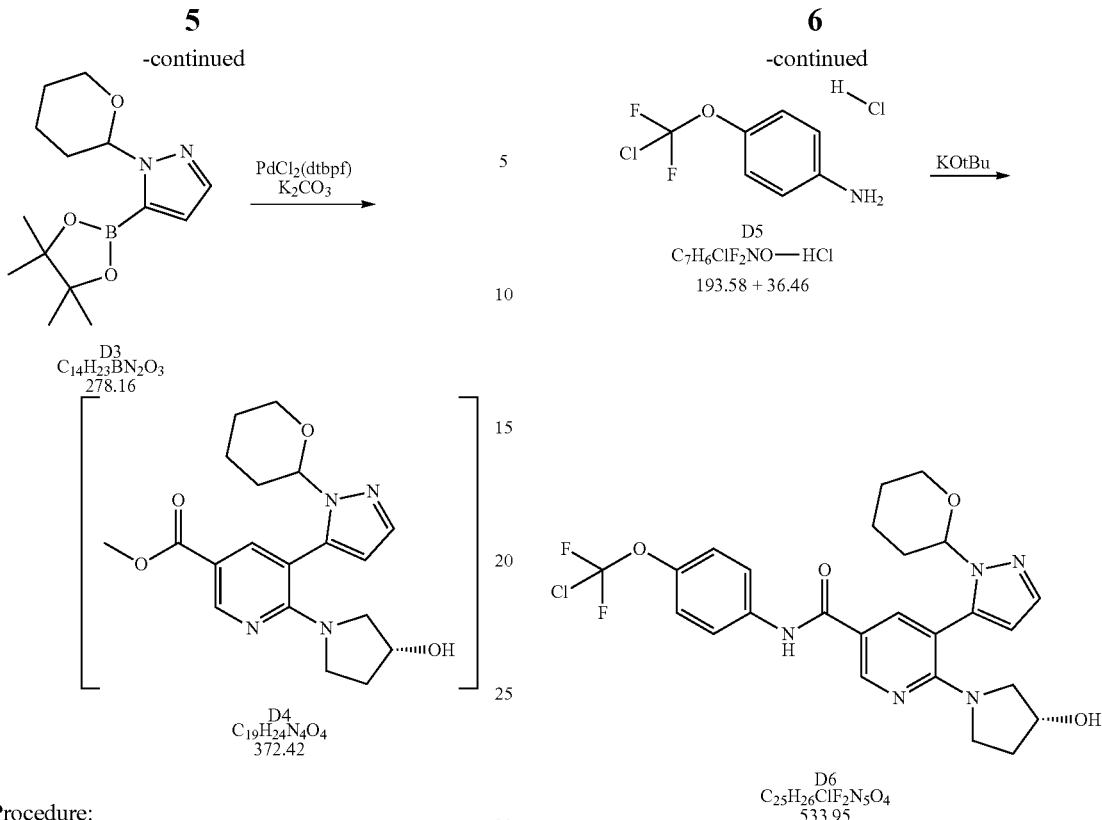

Basic Procedure:

A mixture of (R)-methyl 5-bromo-6-(3-hydroxypyrrolidin-1-yl)nicotinate (45.6 kg, D2), 1-1-(tetrahydro-2H-pyran-2-yl)-1H-pyrazole-5-boronic acid, pinacol ester (50.5 kg, D3), and K$_2$CO$_3$ (41.8 kg) in toluene (282 mL) was added to a dry vessel. The suspension was stirred and water was added. PdCl$_2$(dtbpf) (500 g) was added and the suspension was stirred at about 50° C. until full conversion was achieved. After reaction completion, QuadraSil MP was added to the reaction mixture. The solid residues were removed by filtration over activated charcoal filter and the filter residue was washed with toluene, potable water and again with toluene. The organic and aqueous phases were separated and the aqueous layer was washed with toluene. The combined organic layers were washed with sodium chloride solution, dried using [Na$_2$SO$_4$] and evaporated in situ to provide methyl 6-((R)-3-hydroxypyrrolidin-1-yl)-5-(1-(tetrahydro-2H-pyran-2-yl)-1H-pyrazol-5-yl)nicotinate (D4). Yield of D4 was estimated to be about 54 kg D4/kg D2 (~95%).

Example 2: Step D4+D5→D6

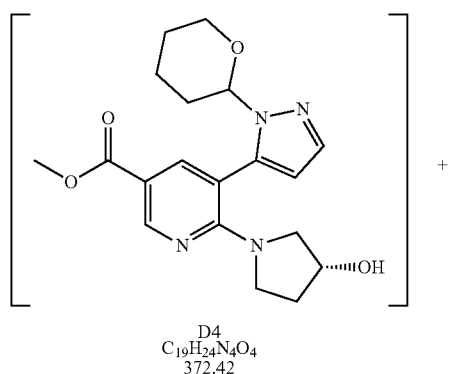

+

To an empty vessel, a solution of sodium hydroxide (15.8 kg) and water was added to a mixture of 31.6 kg 4-(chlorodifluoromethoxy)aniline HCl (D5) in methyltetrahydrofuran (344 kg) and the reaction mixture was stirred at around 25° C. The biphasic mixture was separated and the organic phase was washed twice with water. The organic phase was concentrated by distillation, followed by addition of fresh methyltetrahydrofuran (2×148 kg) to obtain a concentrated solution of 4-(chlorodifluoromethoxy)aniline in methyltetrahydrofuran.

To the 10-20% solution of 660 kg of methyl 6-((R)-3-hydroxypyrrolidin-1-yl)-5-(1-(tetrahydro-2H-pyran-2-yl)-1H-pyrazol-5-yl)nicotinate (D4) in toluene, methyltetrahydrofuran (239 kg) was added and the solution was concentrated by distillation. To this concentrated solution, 148 kg of concentrated solution of D5 in methyltetrahydrofuran was added. To the obtained a mixture, 20% potassium tert-butoxide (258 kg) in tetrahydrofuran (169 kg) was dosed at around 25° C. After reaction completion, aqueous sodium chloride solution (602 kg) was added and biphasic mixture was separated. The organic phase was extracted with aqueous sodium chloride (602 kg) solution. The organic layer was filtered over activated charcoal filter. The solvent was exchanged by distillation from methyltetrahydrofuran to isopropanol. To this solution, seed crystals of N-(4-(Chlorodifluoromethoxy)phenyl)-6-((R)-3-hydroxypyrrolidin-1-yl)-5-(1-(tetrahydro-2H-pyran-2-yl)-1H-pyrazol-5-yl)nicotinamide (0.16 kg, D6) were added, followed by n-heptane (1274 kg). D6 was collected by filtration, washed with a mixture of n-heptane and isopropanol and dried under vacuum. Yield of D6 was estimated to be about 79-87% of D6 based on amount of D3 charged.

Example 3: Step D6→A1

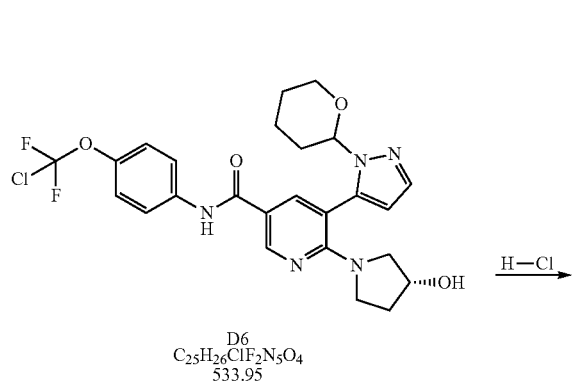

D6
C25H26ClF2N5O4
533.95

H—Cl ↓

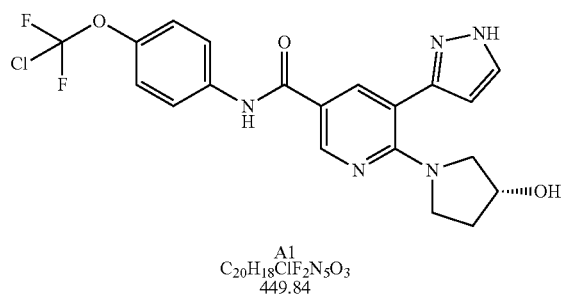

A1
C20H18ClF2N5O3
449.84

To a suspension of N-(4-(Chlorodifluoromethoxy)phenyl)-6-((R)-3-hydroxypyrrolidin-1-yl)-5-(1-(tetrahydro-2H-pyran-2-yl)-1H-pyrazol-5-yl)nicotinamide (39.1 kg, D6) in methanol (346 kg), 37% HCl solution (9 kg) was added at 22° C. (pH<1). The clear solution was then stirred for 1 h at 22° C. (IPC). The mixture was then quenched with 30% NaOH (4 kg) (pH=10). Water was added to the mixture and the pH was adjusted to 2.5 to 3.0 by the addition of 30% NaOH. The solution was filtered over an active charcoal filter and then the pH was adjusted to 3.0-3.5 by the addition of more 30% sodium hydroxide before seeding with N-(4-(Chlorodifluoromethoxy)phenyl)-6-(3-hydroxypyrrolidin-1-yl)-5-(1H-pyrazol-5-yl)nicotinamide (0.027 kg, A1). A final pH adjustment to pH 7.5-9.0 was performed by the addition of ca. 1% sodium hydroxide solution resulting in precipitation of the product. The suspension was cooled to 10° C. and stirred before the product A1 was isolated by filtration, washed with a 4:1 mixture of water/methanol and dried. Yield of A1 was estimated to be about 76%.

Example 4: A1→A1a

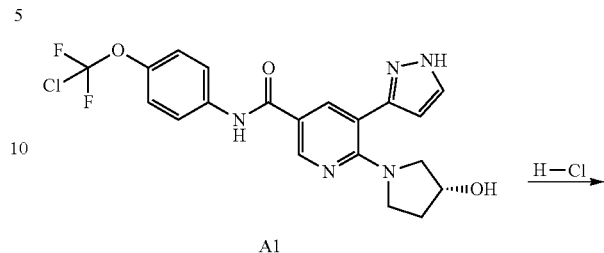

A1
C20H18ClF2N5O3
449.84

H—Cl ↓

A1a
C20H18ClF2N5O3—HCl
449.84 + 36.46

A mixture of N-(4-(Chlorodifluoromethoxy)phenyl)-6-(3-hydroxypyrrolidin-1-yl)-5-(1H-pyrazol-5-yl)nicotinamide (29.2 kg, A1), methanol (190 kg), and 37% hydrochloric acid (7 kg) is heated to about 50° C. and the resulting solution was filtered. The first portion of t-butyl methyl ether TBME (146 kg) and seed crystals of N-(4-(Chlorodifluoromethoxy)phenyl)-6-(3-hydroxypyrrolidin-1-yl)-5-(1H-pyrazol-5-yl)nicotinamide hydrochloride (0.26 kg, A1a) were added at about 50° C. to the filtrate. The second portion of TBME (271 kg) was added and the suspension cooled to about 0° C. and stirred to allow for completion of crystallization. A1a was collected by filtration, washed with a mixture of TBME (78 kg) and methanol (9 kg) and dried under vacuum. Yield of A1a was estimated to be about 96%.

The invention claimed is:

1. A process for producing the compound of formula (1),

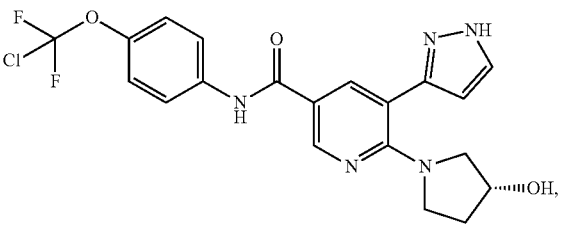

or a salt thereof, comprising the step of reacting the compound of formula (2),

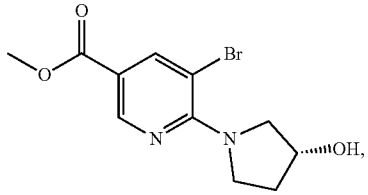

(2)

or a salt thereof;
and the compound of formula (3),

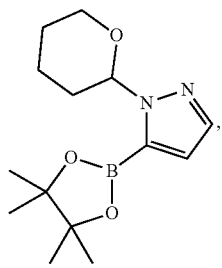

(3)

with an alkali or alkaline salt in the presence of a metal complex catalyst to obtain the compound of formula (1) or a salt thereof, wherein the alkali or alkaline salt is K₂CO₃ and the metal complex catalyst is (dtbpf)PdCl₂.

2. A process according to claim 1, further comprising the step of reacting the compound of formula (4),

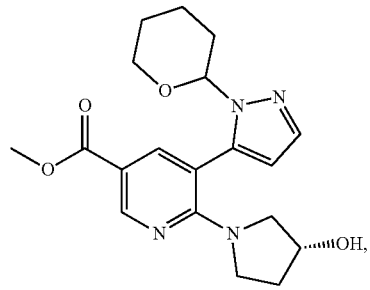

(4)

or a salt thereof, with the compound of formula (5),

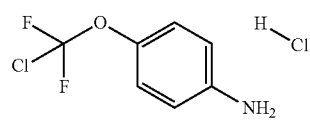

(5)

or a salt thereof.

* * * * *